United States Patent [19]

Krantz et al.

[11] Patent Number: 4,568,184

[45] Date of Patent: Feb. 4, 1986

[54] READER CARD FOR DENSITOMETRIC TEST ANALYSIS

[75] Inventors: Gary B. Krantz, Reseda; Christopher A. Conde, Los Angeles, both of Calif.

[73] Assignee: Mast Immunosystems Ltd., Mountain View, Calif.

[21] Appl. No.: 483,291

[22] Filed: Apr. 8, 1983

[51] Int. Cl.[4] .................... G01N 21/01; G01N 21/25
[52] U.S. Cl. .................................. 356/243; 356/244; 356/443; 422/58
[58] Field of Search ............... 356/243, 444, 443, 244; 250/559, 303, 475.2; 422/55, 56, 57, 58; 235/487, 495; 350/536; 40/158 R

[56] References Cited

U.S. PATENT DOCUMENTS

| | | | |
|---|---|---|---|
| 3,551,023 | 12/1970 | Brackett | 356/244 X |
| 3,705,294 | 12/1972 | Kuehnle et al. | 235/495 X |
| 3,990,850 | 11/1976 | Friedman et al. | 422/55 X |
| 3,997,992 | 12/1976 | Anderson | 40/158 X |
| 4,174,178 | 11/1979 | Ouchi et al. | 356/244 X |
| 4,180,741 | 12/1979 | Palmatier et al. | 356/444 X |
| 4,365,895 | 12/1982 | Shaber et al. | 250/559 X |

OTHER PUBLICATIONS

Robert F. Ritchie, "Clinical Use of Automated Precipitin Data: A Problem of Volume and Physician Acceptance", Advances in Automated Analysis, Technicon International Congress 1970, vol. 1, p. 128.

*Primary Examiner*—Vincent P. McGraw
*Assistant Examiner*—Robert D. V. Thompson
*Attorney, Agent, or Firm*—Fulwider, Patton, Rieber, Lee & Utecht

[57] ABSTRACT

A reader card for use in densitometric test analysis wherein a film having data recorded as spots thereon is supported by and retained on a base card, the reader card further having an area for use in establishing initial conditions for the optical system of the densitometer and a series of borders for indicating the relative position of the film on the card to the optical system of the densitometer. In a preferred embodiment, the reader card includes a base card having an opening therethrough, and an overlay thereover. The overlay retains the film in place and includes a black band covering the film, the black band having windows therethrough for observing and measuring the spots.

10 Claims, 4 Drawing Figures

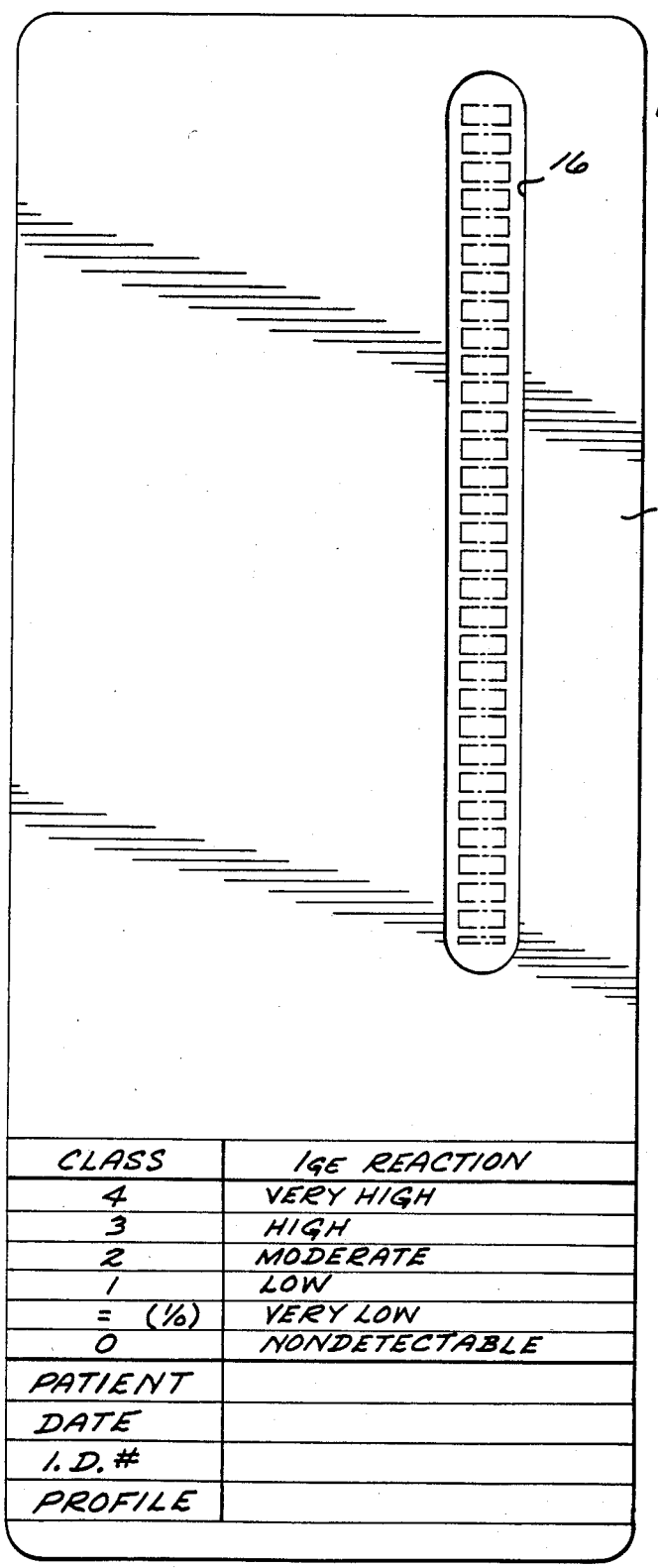
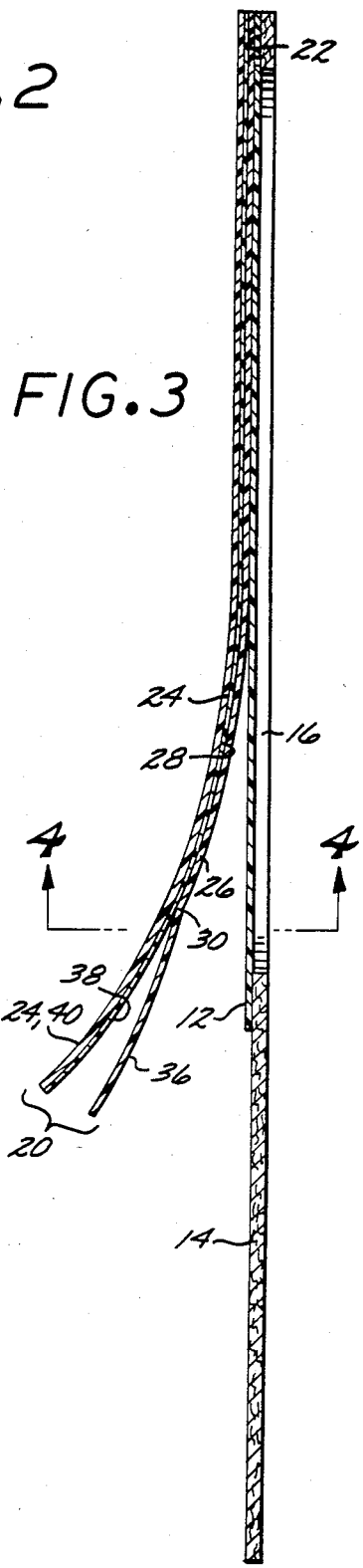

READER CARD FOR DENSITOMETRIC TEST ANALYSIS

BACKGROUND OF THE INVENTION

This invention relates to data measurements, and more particularly, to an article useful in measuring and preserving a film record having immunological data recorded thereon.

One aspect of the field of immunology involves the testing of persons to determine their allergic sensitivity to various substances commonly encountered, such as pollen and animal fur. In an early test to determine sensitivity to various allergens, a sample of the suspected allergen was placed on a patch and the patch was then placed in contact with the person's skin. After several days, the patch was removed and the skin examined to determine the presence of any allergic reaction. This qualitative test is subject to numerous inaccuracies, and only one or a few tests can be performed at once.

In a new test for determining allergic reactions, other immunological reactions, or other microbiological interactions, an insoluble carrier coated with a known quantity of a single antigen such as that found in an allergen can be exposed to, and incubated in, a sample of the patient's blood serum. If the patient is allergic to the particular antigen, a measurable binding reaction occurs during the incubation. A variety of techniques can be utilized to measure the extent of such reaction, and one such technique involves the use of a radioimmunoassay, in which the carrier is incubated with a liquid containing radioactively-tagged molecules that bind to any serum antibody previously bond to the antigen-coated carrier during the incubation. The presence of any radioactivity on a particular region of the carrier can then be measured as, for example, by means of a gamma counter or, alternatively, by exposing photographic film and then measuring the optical density of a resulting photographic print. A commonly assigned U.S. Pat. No. 4,459,360 describes this incubation and measurement technique in greater detail.

One advantage of this latter technique is that the extent of the reaction to a large number of antigens may be determined in a single test using less than two milliliters of blood serum. For example, on a piece of film about 4.5 inches long, the results of as many as 27 tests may be recorded as a series of longitudinally spaced-apart spots or stripes. Additionally, calibration data may be recorded on the film.

As described in a concurrently filed and commonly-assigned application for U.S. Pat. Ser. No. 483,292, filed April 8, 1983 in the names of Vincent A. Marinkovich, et al and entitled "Reaction Measurement System"; instrumentation has been developed for reading and measuring the test data recorded on the film automatically and rapidly, from a film print or negative. However, as a necessary part of this system the film must be properly presented to the instrumentation for analysis, in a manner wherein the apparatus is automatically activated and is calibrated in conjunction with the conditions of presentation. The film should be presented in a way allowing the apparatus to individually analyze and report the results corresponding to each reaction spot. Finally, the presentation means should allow the film to be readily examined visually by medical personnel and provide for the permanent preservation of the film in the person's medical file.

Accordingly, there is a need for an article which may be used to present a data record such as photographic film to apparatus wherein the optical density of the individual spots or stripes thereon is measured, and further having the desirable features set forth above. The present invention fulfills this need, and further provides related advantages.

SUMMARY OF THE INVENTION

The present invention resides in a reader card for presenting a data record such as photographic film to an analytical instrument wherein the density of spots or stripes on the film is determined as a measure of the extent of a chemical reaction. When used in conjunction with an instrument having an optical densitometer, the reader card presents the data record in a manner which activates the instrument and allows the instrument to be automatically calibrated both as to an initial low light level and also as to nonspecific binding produced during the incubation procedure. The data presentation provides for the recording of test information and storage of a data report from the instrument, the data report preferably being a paper tape setting forth the test results. The reader card also stores the film, the data report, and supporting test information in a single convenient format, for storage in the patient's files.

More specifically, a reader card in accordance with the invention comprises a data record support and associated indexing means for initializing the densitometer and for indicating the positioning of the card relative to the light sensor of the densitometer, and further having retaining means for positioning and retaining the data record on the data record support in viewable registration with the indexing means. A data record such as a piece of film supported by the data presentation card is inserted into the densitometer, whereupon the instrumentation is activated, the light sensing instrumentation of the densitometer is initialized to a low light level, and the separate spots or stripes on the film are serially presented to the light sensor for detection and analysis. Data from each measurement is then processed for display.

In a preferred embodiment of the invention, the reader card comprises a base card having an elongated opening therethrough with a lengthwise dimension sufficiently great that the spots on the film are visible through the opening when the film is overlaid onto the card. A plastic overlay is bonded to one end of the base card, so that the film may be positioned between the base card and the overlay, with the spots over the opening in the base card. An opaque, preferably black, band having a plurality of longitudinally spaced-apart transparent windows therethrough is printed onto the overlay, the windows being disposed and dimensioned for individually registering over the spots on the film, whereby each spot may be viewed by light passing through the base card opening and the window associated with the spot. The preferred reader card further includes means for retaining the film in registry with the window and the opening, preferably comprising a pocket formed between the overlay and the base card by two adhesive strips parallel to and laterally spaced apart from the opening of the base card, an adhesive strip at one end of the base card, and a sealable opening at the other end of the film through which the film is inserted prior to sealing.

It will be appreciated that the present invention represents an advance in the field of partially automated fluid testing, particularly when used in conjunction with the associated automated densitometer described in the above referenced patent application. With this card for presentation of film to the densitometer, the film may be measured and analyzed in an automated fashion, and the results immediately displayed. The present invention and the related inventions thereby together provide a significant advance in the detection and analysis of fluid reactions. Other features and advantages of the present invention will become apparent from the following more detailed description taken in conjunction with the accompanying drawings, which illustrate, by way of example, the principles of the invention.

BRIEF DESCRIPTION OF THE DRAWINGS

The accompanying drawings illustrate a preferred embodiment of the invention. In such drawings:

FIG. 2 is a plan view generally similar to that of FIG. 1, except with the overlay removed, and with a piece of film shown in phantom lines;

FIG. 3 is a longitudinal sectional view through the reader card, taken generally along line 3—3 of FIG. 1; and FIG. 4 is an enlarged fragmented transverse sectional view of the reader card, taken generally along line 4—4 of FIG. 3.

DETAILED DESCRIPTION OF THE PREFERRED EMBODIMENT

Figure 1:
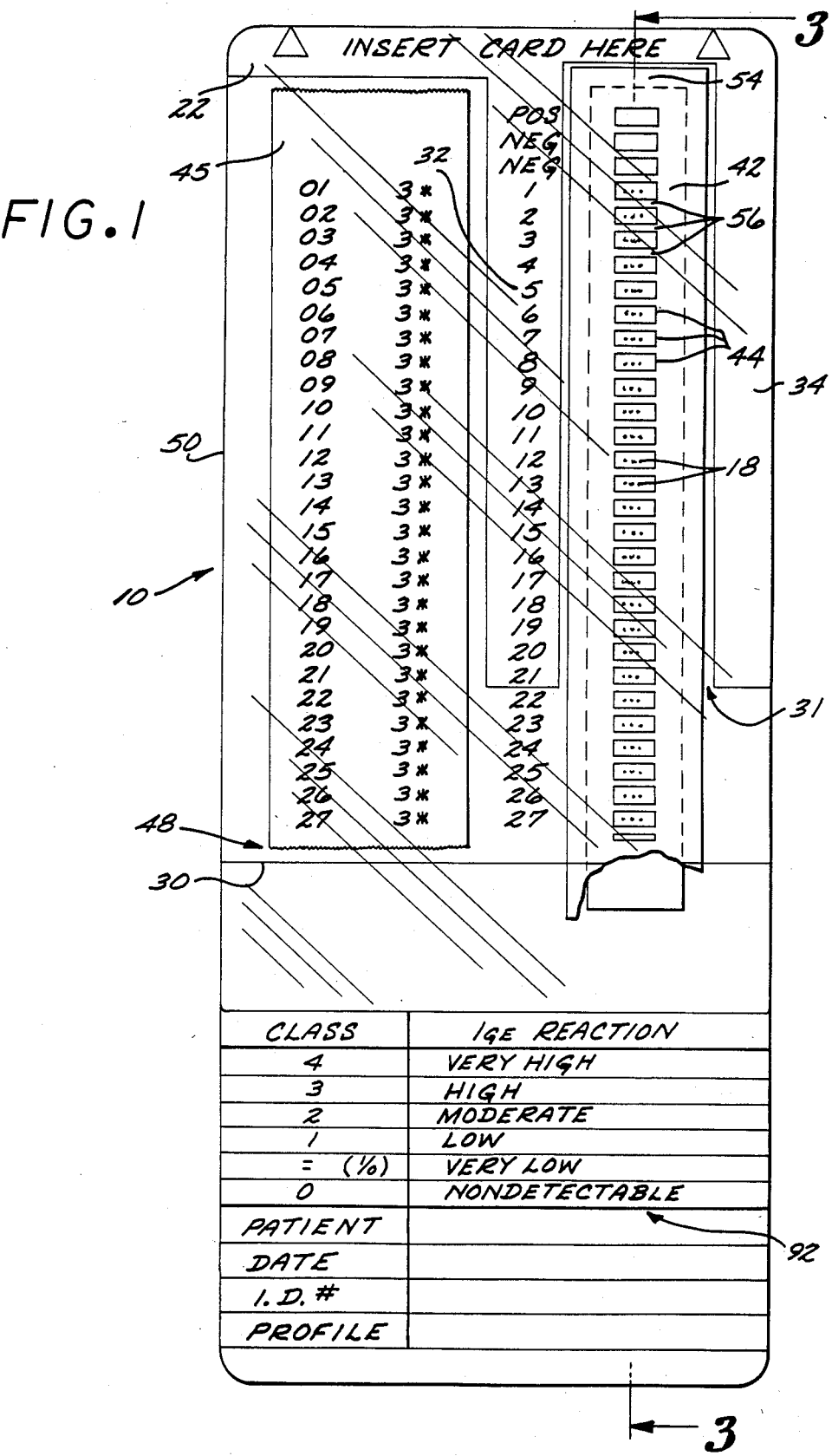
FIG. 1 is a plan view of a reader card, illustrating a base card and an overlay.

As is shown in the drawings for purposes of illustration, the invention is embodied in a reader card 10 for mounting and presenting a piece of film 12 to a reading device (not shown). The procedure for preparing the film 12 is set forth in U.S. Pat. No. 4,459,360, which disclosure is incorporated herein by reference. The film 12 is about ¾ inch wide by 4¾ inch long, having a plurality of longitudinally spaced-apart stations whereat levels of reactivity are recorded as a series of spots. The film 12 is preferably developed as a positive print, so that the lowest levels of reactivity are recorded as nearly black regions, and increasing reactivities are evidenced by spots which are increasingly white and intense with increasing immunological activity.

The film 12 is mounted in the reader card 10 for supporting the film for subsequent analysis in a densitometer (not shown). A process for analysis of the data and a preferred densitometer structure are disclosed in a concurrently-filed and commonly-assigned application for U.S. Pat. Ser. No. 483,292, filed in the name of Vincent A. Marinkovich, et al and entitled "Reaction Measurement System", which disclosure is incorporated herein by reference. Briefly, the densitometer includes a light source and a light sensor, disposed on either side of the plane of the film when it is inserted into the densitometer and positioned so that a beam of light from the light source passes through the film for detection of the intensities of individual spots by the sensor. A drive mechanism transports the film past the light source and sensor in a direction parallel to the longitudinal spacings of the spots so that the spots are analyzed individually and sequentially by the sensor. Microcomputer circuitry in the densitometer processes the signal from the sensor into classifications meaningful to the users for display on a monitor or printing on a paper tape.

In accordance with the invention, the reader card 10 includes a base card 14 for receiving and supporting the film 12. An elongated opening 16 extends through the thickness of a portion of the base card 14, the opening 16 being elongated in the direction parallel to the direction of insertion. The length and width of the opening 16 are sufficient to include within the projection of its boundaries all of a plurality of spots 18 on the film 12, when the film 12 is properly positioned over the opening 16, as shown in FIG. 2.

An overlay 20 is bonded to the base card 14, preferably at a top adhesive strip 22 along the edge of the base card 14 first inserted into the densitometer. The overlay 20 overlies at least a portion of the base card 14, including the opening 16. The overlay 20 is transparent, except as hereinbelow described, and includes a transparent top ply 24, a transparent bottom ply 26, and a pressure sensitive adhesive interlayer 28 bonding the top ply 24 to the bottom ply 26. A parting line 30 is scored across the full width of the bottom ply 26, so that a portion of the bottom ply 26 may be peeled away to expose the adhesive interlayer 28 on the underside the the top ply 24, over a portion of the underside of the overlay 20. Preferably, both plies 24 and 26 are formed of Mylar plastic.

A pocket 31 between the overlay 20 and the base card 14 is formed adjacent the opening 16 to receive and position the film 12, with all of the spots 18 within the projection of the boundaries of the opening 16. One end of the pocket 31 is formed by the top adhesive strip 22, and the sides of the pocket 31 are formed by a first side adhesive strip 32 and a second side adhesive strip 34, each strip 32 and 34 joining the overlay 20 to the base card 14 along a strip parallel to, but spaced-apart laterally from, the elongated sides of the opening 16. The strips 32 and 34 are spaced apart laterally from the edges of the opening 16 a distance sufficient to receive the film 12 into the pocket 31 upon insertion from the remaining open side of the pocket 31.

The film 12 may be sealed into the pocket 31 by first removing a peel strip 36 from the bottom ply 26 of the overlay 20 by tearing the peel strip 36 along the parting line 30. Removal of the peel strip 36 exposes a bottom adhesive strip 38 on the underside of the top ply 24, thereby creating a bottom closure 40. The pocket 31 for receiving the film 12 is then closed on the remaining side by adhering the underside of the bottom closure 40 to the top surface of the base card 14 along the bottom adhesive strip 38 to seal the film 12 into the pocket 31.

An elongated black band 42 is imprinted on the overlay 20 to cover at least the opening 16 and preferably most of the pocket 31. The black band 42 may be conveniently silkscreened onto the overlay 20 by conventional techniques. The black band 42 should be opaque to light from the light source of the densitometer.

A plurality of longitudinally spaced apart transparent windows 44 open through the black band 42, the plurality of windows 44 being dimensioned and disposed to registerably frame the plurality of spots 18 when the film 12 is inserted into the pocket 31 so that each spot 18 is visible through a single window 44. Each spot 18 of the film 12 overlies a portion of the opening 16 and in turn is framed by the black border of the band 42 around the individually registered windows 44.

Thus arranged, the intensity levels of the individual spots 18 may be detected, measured, and analyzed by light passing through the film 12 in the densitometer. After the results of the analysis are printed, a paper data tape 45 recording the results may be inserted into the reaction card 10 in a second pocket 48 having sides defined by the top adhesive strip 22, the first side adhesive strip 32, and the bottom adhesive strip 38, and accessible through a tape opening 50. No further side closure of the tape opening 46 is required, as the precise positioning of the data tape 45 is not critical. As assembled, the reader card 10 permanently stores in a convenient form the film 12, the data tape 45, and a written test identification 52 for storage in the file of the patient. The test results may be later conveniently reviewed visually by the users, as desired.

To analyze test results using the reader card 10 in conjunction with the densitometer for automated analysis, the film 12 is first positioned and sealed into the pocket 31 in the manner described previously. The reader card 10 is inserted into the densitometer, until the light beam of the light sensor is interrupted by the black band 42, with the light sensor being positioned above a black level calibration area 54 at the end of the black band 42 nearest the end of the reader card 10 first inserted into the densitometer. Because no light is transmitted to the sensor from the light source, a "black level" for optical calibration is thereby provided. Upon completion of this calibration step, the densitometer activates its drive mechanism to move the card 12 forwardly so that the film spot 18 framed by the first window 44, denoted "POS" in FIG. 1, is moved past the optical sensor for measurement.

Upon passing over the full width of the first window 44, the optical sensor encounters a border 56 portion of the black band 42 between the first and second windows. The border 56 is opaque and therefore exhibits a light level approximately that of the black level calibration area 54, whereupon the logic circuit of the densitometer halts forward motion of the drive mechanism to allow computations, display, and printing of information, as required. The spots appearing in the first three openings of the preferred standardized film format provide test acceptability, calibration and normalization information, and no results are displayed or printed. Reactivity levels are determined from the remaining film spots. Upon completion of each analysis and printing cycle, the drive mechanism is reactivated to move the spot 18 framed to the next window 44 past the light sensor. Operation of the densitometer and its analysis functions are presented in more detail in the copending application entitled "Reaction Measurement System" referenced above.

It will now be appreciated that through the use of this invention and related inventions described and referenced hereinabove, testing such as allergy sensitivity testing may be readily and economically accomplished. The reader card of the present invention allows photographic film having a series of spots whose intensities are related to reactivity to be registerably mounted for automated analysis in a densitometer. Elements of the reader card cooperate with the light sensor and logical programming of the densitometer to provide automated optical calibration, reaction calibration and normalization, indication of test acceptability, and sequential measuring, calculation and presentation of the results of a plurality of tests. Although a particular embodiment of the invention has been described in detail for purposes of illustration, various modifications may be made without departing from the spirit and scope of the invention. Accordingly, the invention is not to be limited except as by the appended claims.

We claim:

1. A reader card used in analyzing previously exposed photographic film, the film having thereon a plurality of longitudinally spaced-apart spots whose intensities vary in accordance with a response level to a testing procedure, comprising:
   a base card having an opening therethrough, the opening being dimensioned so that the spots on the film lie within the projection of said opening when the film is placed onto said base card;
   an overlay over at least a portion of said base card;
   an opaque band on said overlay, said band covering said opening; and
   a plurality of longitudinally spaced-apart, transparent windows through said opaque band, each of said windows being dimensioned and disposed for registration over the film so that the spots on the film are individually viewable in light passing through said opening and said window; and
   means for retaining the film in registration with said windows and overlying said opening.

2. The reader card of claim 1, wherein said means for retaining the film is a pocket formed between said base card and said overlay.

3. The reader card of claim 1, wherein said overlay is constructed by a transparent plastic material.

4. The reader card of claim 1, wherein the spots on the data record indicate allergic sensitivities.

5. The reader card of claim 1, wherein said opaque band has about thirty windows therethrough.

6. The reader card of claim 1, wherein said overlay is constructed of at least two plies of a transparent plastic material with an adhesive between said plies.

7. The reader card of claim 1, wherein said opaque band is black.

8. A reader card for use in analyzing previously exposed photographic film, the film having thereon a plurality of longitudinally spaced-apart spots whose intensities vary in accordance with a response level to an immunological testing procedure, comprising:
   an elongated cardboard base card having an opening therethrough, said opening being elongated in the same direction as said base card, said opening being dimensioned so that the spots on the film lie within the projection of said opening when the film is placed onto said base card;
   a transparent overlay joined to said base card along one edge thereof and also joined to said base card along a pair of strips parallel to but spaced-apart from the sides of said opening, the three regions of joinder, said base card and said overlay together defining a pocket for receiving the film, said overlay having two plies and an adhesive layer therebetween, a portion of the ply adjacent the base card being removable to expose the adhesive so that said overlay may be adhesively joined to said base card along a fourth region of joinder to close said pocket after the film is inserted therein;
   a black band inprinted on said overlay, said band being dimensioned and disposed to cover at least said opening; and
   a plurality of longitudinally spaced-apart, transparent windows through said black band, each of said windows being disposed for registration over a separate spot on the film and being dimensioned so that the spot is visible through said window.

9. The reader card of claim 8, wherein one dimension of said card is about 3¼ inches.

10. The reader card of claim 8, wherein the plies of said overlay are formed of a transparent plastic film.

* * * * *